US010603252B2

(12) United States Patent
Kim et al.

(10) Patent No.: US 10,603,252 B2
(45) Date of Patent: Mar. 31, 2020

(54) TOOTH-ATTACHABLE PATCH CAPABLE OF BEING REMOVED BY TOOTH BRUSHING

(71) Applicant: LG Household & Health Care Ltd., Seoul (KR)

(72) Inventors: Jong-Hoon Kim, Daejeon (KR); Jae-Hyun Ahn, Daejeon (KR); Kwang-Ho Oh, Daejeon (KR); In-Ho Lee, Daejeon (KR)

(73) Assignee: LG Household & Health Care Ltd. (KR)

( * ) Notice: Subject to any disclaimer, the term of this patent is extended or adjusted under 35 U.S.C. 154(b) by 0 days.

(21) Appl. No.: 15/758,650

(22) PCT Filed: Aug. 30, 2016

(86) PCT No.: PCT/KR2016/009662
§ 371 (c)(1),
(2) Date: Mar. 8, 2018

(87) PCT Pub. No.: WO2017/043800
PCT Pub. Date: Mar. 16, 2017

(65) Prior Publication Data
US 2018/0250203 A1    Sep. 6, 2018

(30) Foreign Application Priority Data

Sep. 9, 2015 (KR) .................. 10-2015-0127721
Oct. 6, 2015 (KR) .................. 10-2015-0140101
Oct. 6, 2015 (KR) .................. 10-2015-0140104

(51) Int. Cl.
*A61K 8/02* (2006.01)
*A61K 33/40* (2006.01)
*A61C 19/06* (2006.01)
*A61K 47/38* (2006.01)
*A61K 9/70* (2006.01)
*A61K 9/00* (2006.01)
*A61K 47/32* (2006.01)
*A61K 36/899* (2006.01)
*A61K 8/9794* (2017.01)
*A61J 7/00* (2006.01)
*A61K 8/19* (2006.01)
*A61K 8/22* (2006.01)
*A61K 8/24* (2006.01)
*A61K 8/73* (2006.01)
*A61Q 11/00* (2006.01)

(52) U.S. Cl.
CPC ............ *A61K 8/0208* (2013.01); *A61C 19/06* (2013.01); *A61C 19/063* (2013.01); *A61C 19/066* (2013.01); *A61J 7/0092* (2013.01); *A61K 8/19* (2013.01); *A61K 8/22* (2013.01); *A61K 8/24* (2013.01); *A61K 8/731* (2013.01); *A61K 8/9794* (2017.08); *A61K 9/006* (2013.01); *A61K 9/7007* (2013.01); *A61K 9/7053* (2013.01); *A61K 33/40* (2013.01); *A61K 36/899* (2013.01); *A61K 47/32* (2013.01); *A61K 47/38* (2013.01); *A61Q 11/00* (2013.01); *A61K 2800/5922* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 6,375,963 | B1 | 4/2002 | Repka et al. |
| 6,682,721 | B2 | 1/2004 | Kim et al. |
| 6,689,344 | B2 | 2/2004 | Chang et al. |
| 6,780,401 | B2 | 8/2004 | Kim et al. |
| 2003/0124178 | A1 | 7/2003 | Haley |
| 2003/0194382 | A1* | 10/2003 | Chang .................. A61K 8/0208 424/53 |
| 2004/0033205 | A1 | 2/2004 | Date et al. |
| 2004/0057910 | A1 | 3/2004 | Lee et al. |
| 2004/0180080 | A1 | 9/2004 | Furusawa et al. |
| 2004/0219113 | A1 | 11/2004 | Choi et al. |
| 2005/0232982 | A1 | 10/2005 | Ihara et al. |
| 2006/0018845 | A1 | 1/2006 | Edelstein et al. |
| 2006/0073174 | A1 | 4/2006 | Moro et al. |
| 2006/0099550 | A1 | 5/2006 | Faasse et al. |
| 2012/0100192 | A1 | 4/2012 | Penhasi et al. |

FOREIGN PATENT DOCUMENTS

| | | |
|---|---|---|
| CN | 104013536 A | 9/2014 |
| JP | 2006505614 A | 2/2006 |
| KR | 20030031511 A | 4/2003 |
| KR | 20040000784 A | 1/2004 |
| KR | 100440241 B1 | 7/2004 |
| KR | 100458337 B1 | 12/2004 |
| KR | 20050072086 A | 7/2005 |
| KR | 20050082187 A | 8/2005 |

(Continued)

OTHER PUBLICATIONS

Search report from International Application No. PCT/KR2016/009662, dated Jan. 11, 2017.

(Continued)

*Primary Examiner* — Celeste A Roney

(74) *Attorney, Agent, or Firm* — Lerner, David, Littenberg, Krumholz & Mentlik, LLP

(57) ABSTRACT

The present invention relates to a tooth-attachable patch comprising: a drug layer for delivering drugs to a tooth; and a backing layer positioned on the opposite side of a tooth attachment surface of the drug layer, and including, both a water-soluble polymer and a water-insoluble polymer. The patch of the present invention can be easily removed by merely brushing the teeth without separately stripping off a backing layer.

18 Claims, 7 Drawing Sheets

(56) References Cited

FOREIGN PATENT DOCUMENTS

| | | |
|---|---|---|
| KR | 20050119914 A | 12/2005 |
| KR | 20060094713 A | 8/2006 |
| KR | 20060097172 A | 9/2006 |
| KR | 20060097177 A | 9/2006 |
| KR | 100648022 B1 | 11/2006 |
| KR | 100755765 B1 | 9/2007 |
| KR | 100816250 B1 | 3/2008 |
| KR | 101148470 B1 | 5/2012 |
| KR | 20150111667 A | 10/2015 |
| KR | 20150118784 A | 10/2015 |
| WO | 2002074275 A2 | 9/2002 |
| WO | 2013039495 A1 | 3/2013 |

OTHER PUBLICATIONS

Extended European Search Report for Application No. EP16844620.1 dated Mar. 28, 2019.
Search report from International Application No. PCT/KR2016/009666, dated Dec. 13, 2016.

* cited by examiner (a)  (b)

(a)

(b)

TOOTH-ATTACHABLE PATCH CAPABLE OF BEING REMOVED BY TOOTH BRUSHING

CROSS-REFERENCE TO RELATED APPLICATIONS

This application is a national phase entry under 35 U.S.C. § 371 of International Application No. PCT/KR2016/009662, filed Aug. 30, 2016, which claims priority to Korean Patent Application No. 10-2015-0127721 filed Sep. 9, 2015, Korean Patent Application No. 10-2015-0140101 filed Oct. 6, 2015, and Korean Patent Application No. 10-2015-0140104 filed Oct. 6, 2015, the disclosures of which are incorporated herein by reference.

TECHNICAL FIELD

The present invention relates to a tooth-attachable patch capable of being removed by tooth brushing, and more specifically, it relates to a tooth-attachable patch which can be easily removed by tooth brushing alone without stripping off a backing layer supporting a drug layer.

BACKGROUND ART

Procedures such as whitening of teeth have been performed mainly in dentistry in the past, hut since dental procedures are cumbersome and very expensive, there have been a lot of developments in recent years for easy-to-use products.

There are products such as toothpaste, mouth rinse, chewing gum, oral tray, gel for tooth application, and mouth patch for selection of teeth whitening, but patch type products are used most in consideration of convenience of use.

A tooth-attachable patch generally has a structure including a drug layer containing a drug for the purpose of use, such as a drug for tooth whitening, a drug for preventing or improving sensitive teeth, and a backing layer for selectively delivering the drug component to teeth.

Korean Patent No. 10-0458337 suggests manufacturing the backing layer to be water-insoluble, so as to selectively deliver the drug component contained in the patch only to teeth. However, the patch including such water-insoluble backing layer is cumbersome to remove the remaining backing layer after use. Meanwhile, if the patch is removed by tooth brushing alone without stripping off the patch, the undegraded film lumps will become clogged in a toothbrush, making it difficult to remove it from the toothbrush. As a product improving this problem, a product which is dissolved in the oral cavity after patch attachment was developed, but the drug component was not selectively delivered to teeth and mixed with the saliva, resulting in the problem that the intended drug effect was not expressed.

Meanwhile, the inventors of the present invention have studied for a long time that a patch cannot be degraded by saliva or water during use but can be easily removed by tooth brushing after use. Furthermore, the inventors of the present invention have completed the present invention by studying a method for easily removing the patch by tooth brushing, and also particularly removing thereof without foreign body sensation in the mouth due to small size of the disassembled pieces.

DISCLOSURE

Technical Problem

Accordingly, in order to solve the above problem, the present invention is directed to providing a tooth-attachable patch, which can be easily removed from the surface of teeth by tooth brushing alone without clotting of undegraded film lumps between brushes of a toothbrush.

The present invention is directed to providing a convenient tooth-attachable patch, which can be simply removed by tooth brushing alone without any separate residue after use.

Further, the present invention is directed to providing a patch for attaching to teeth or a surrounding part of teeth capable of being easily degraded or removed by tooth brushing, which has especially excellent removability and provides excellent use sensation without foreign body sensation due to small size of disassembled particles.

These and other objects and advantages of the present invention may be understood from the following detailed description and will become more fully apparent from the exemplary embodiments of the present invention. Also, it will be easily understood that the objects and advantages of the present invention may be realized by the means shown in the appended claims and combinations thereof.

Technical Solution

In order to achieve the above objects, the present inventors found that when a patch for attaching to teeth or a surrounding part of teeth 1 is designed to make a drug of a drug layer 10 be selectively delivered only to the surface of teeth, and to make a backing layer 20 of the tooth-attachable patch, which plays a role of keeping the patch shape constant, include both a water-soluble polymer and a water-insoluble polymer, the patch can be easily degraded and removed by pressure such as brushing after use, thereby completing the present invention.

Most patch-type drug delivery systems, especially tooth-attachable patches, are equipped with a backing layer to allow specific drug delivery to the target site. The backing layer is made of a polymer that is not soluble in water or saliva and can maintain its shape even when attached to the teeth. And, when the medicinal ingredients are released and delivered to teeth after being attached to teeth, the backing layer make the medicinal ingredients be released only in the direction of teeth. Namely, it was common to produce the backing layer water-impermeable or water-insoluble in order to selectively deliver the drug in the direction of teeth and prevent the drug from diluting with saliva or water.

Such water-impermeable or water-insoluble backing layer had to be stripped off from the surface of teeth after using the patch.

After removing the backing layer after use, in order to remove the residue remained in the surface of teeth, teeth should be brushed. Accordingly, the inventors of the present invention studied about a way to deliver drugs to the surface of teeth by only tooth brushing without removing the backing layer, and to achieve a perfect finish, thereby completing the present invention.

Namely, the backing layer, which was only made water-insoluble and was being used for a while in the art, was manufactured in the form that can be dissolved by saliva.

Specifically, the inventors of the present invention provides a patch for attaching to teeth or a surrounding part of teeth, which comprises: a drug layer for delivering drugs to teeth; and a backing layer positioned on the opposite side of a tooth attachment surface of the drug layer, and including, both a water-soluble polymer and a water-insoluble polymer.

The drug layer may include drugs to be delivered to teeth. The drugs may preferably be delivered to the surface of teeth, and examples of the drugs may include ingredients for whitening teeth, ingredients for preventing or improving sensitive teeth, ingredients for preventing or improving periodontal disease such as periodontitis and gingivitis, or ingredients for preventing cavities.

The ingredients for whitening teeth may be peroxides, polyphosphates, enzymes, chlorinated bleaching agents. The peroxides may be selected from the group consisting of hydrogen peroxide, carbamide peroxide, calcium peroxide, sodium percarbonate, sodium perborate, tetrasodium pyrophosphate peroxidate and a mixture thereof. The phosphates and the enzymes are effective for removing major stains contained in an enamel layer. The polyphosphates may be, for example, at least one selected from the group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), ultra-metaphosphate (acidic sodium meta-polyphosphate) as ultra-phosphate and acidic sodium polyphosphate. In general, polyphosphate is a tartar controlling agent in a toothpaste and known to be effective in inhibiting tartar formation and tartar removal in toothpaste. Further, the polyphosphate is a good metal chelating agent and therefore it can effectively remove tooth stains, especially, formed by metal in foods or working environment such as iron, calcium and magnesium, thereby somewhat contributing to enhance whitening effect. When using the polyphosphate in the preparation according to the present invention, it is expected that not only improvement of whitening effect by removal of light extrinsic stain but also prolongation of contact time between teeth and condensed phosphate is effective in inhibiting tartar formation and tartar removal. The chlorinated bleaching agents may be sodium chlorite, sodium hypochlorite and the like. In addition, papain, vitamin E and sodium bicarbonate also can be used as a whitener.

In another embodiment, the ingredients for preventing or improving sensitive teeth, or preventing cavities may be strontium chloride, calcium carbonate, sodium citrate, sodium fluoride, silica, hydroxyapatite, potassium nitrate, potassium phosphate and the like.

In another embodiment, the drug component may include ingredients for preventing periodontal disease, and the periodontal disease refers to the loss of teeth due to periodontitis, gingivitis and hemorrhage, formation of periodontal pockets, and destruction of alveolar bone. In order to prevent the incidence of the periodontal disease, the drug layer may include bamboo salt, titrated Extract of *Zea Mays* L. unsaponifiable fraction, policresulen, tetracycline, chlorhexidine gluconate, cetyl pyridinium chloride, sanguinarine, triclosan and the like, and also include an extract of herbal medicine such as *Magnoliae Cortex, Centella Asiatica*, Chamomile, Rhatany, Mynha, *Mori Cortex Radicis, Cimicifugae Rhizoma*, Green tea, *Glycyrrhizae Radix et Rhizoma, Scutellariae Radix, Taraxaci Herba*, and *Lonicerae Flos.*

The drug layer is preferably a dry type in which the drug layer has no or weak adhesion strength in a dry condition, but when it is hydrated by a small amount of water at the site where the whitener is desired to function, it begins to have adhesion strength and to release the whitener as it begins to be hydrated. However, it can also be used as a gel type that can be attached to teeth by its own viscosity. The polymer which can be used herein should have hydrophilicity or at least partial hydrophilicity. The polymer typically used may be polyalkyl vinyl ether-maleic acid copolymer (PVM/MA copolymer; Gantrez AN 119, AN 139, S-97), polyvinyl alcohol, polyacrylic acid, Poloxamer 407 (Pluronic, poly (ethylene oxide)-poly(propylene oxide)-poly(ethylene oxide) triblock copolymer), polyethyleneoxide (Polyox), polyvinyl pyrrolidone-vinyl acetate copolymer (PVP/VA copolymer; Luviskol VA, Plasdone S PVP/VA), polyvinyl pyrrolidone (PVP; 120), polyquaternium-11 (Gafquat 755N), polyquaternium-39 (Merquat plus 3330), carboxypolymethylene (Carbomer, Carbopol), hydroxypropyl methyl cellulose, hydroxyethyl cellulose, hydroxypropyl cellulose, starch, gelatin, sodium alginate alone or a mixture thereof. A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

A matter for tooth attachment should be flexible enough to be attached directly to teeth and be easily shaped according to the flexion of teeth. Depending on the polymer, this flexibility may be poor, so a suitable plasticizer may be added. Suitable plasticizer may vary depending on the kind of polymer and its prescription, and polypropylene glycol, glycerin or polyethylene glycol is generally used, and all of them also can be used.

Further, in the drug layer, a chelating agent such as EDTA or sodium citrate may be added for the purpose of improving the temporal stability of peroxide.

The term "drug layer" used herein means a layer containing medicinal ingredients to achieve the goal of a tooth-attachable patch. For example, a patch for tooth whitening means a layer containing tooth whitening ingredients (preferably, hydrogen peroxide, sodium peroxide and the like), and a patch for relieving sensitive teeth means a layer containing ingredients for relieving sensitive teeth such as potassium nitrate, potassium chloride and the like.

It has been recognized in the art that the backing layer, which is used to protect the drug layer from physical or chemical contact such as saliva and contact in the oral cavity or to maintain a product shape is preferably a water-insoluble polymer in order to serve as a backing layer, and it is stripped off after use of the backing layer. However, unlike such common sense in the art, the inventors of the present invention designed a method for using the backing layer, which can be easily removed by simply tooth brushing alone without stripping off the backing layer because the backing layer includes a water-soluble polymer.

The term "backing layer" used herein means a layer playing a role in preventing contact with the skin in the oral cavity other than teeth.

In one embodiment of the present invention, the backing layer may include a water-insoluble polymer generally used in an oral film, and for example, it may be cellulose acetate phthalate, shellac, polyvinyl acetate, ethyl cellulose, polymethyl methacrylate, methacryloyl ethyl betaine/methacrylate copolymer (Yukaformer: manufactured by Mitsubishi), methacrylic acid copolymer (Eudragit L 100, Eudragit L 12.5, Eudragit L 100-55, Eudragit L 30D-55), aminoalkyl methacrylate copolymer (Eudragit E 100, Eudragit E 12.5, Eudragit RL 100, Eudragit RL 30D) and the like. In addition, the backing layer of the patch for attaching to teeth or a surrounding part of teeth of the present invention includes a water-soluble polymer. The term "water-soluble polymer" used herein means a polymer which can be dissolved in water, swelled or dispersed into small particles. A hydrophilic polymer also can be in the same meaning as the water-soluble polymer of the present invention.

The water-soluble polymer may include a water-soluble polymer which can be used in a drug layer. It may be polyalkyl vinyl ether-maleic acid copolymer (PVM/MA copolymer; Gantrez AN 119, AN 139, S-97), polyvinyl alcohol, polyacrylic acid, Poloxamer 407 (Pluronic, poly(ethylene oxide)-poly(propylene oxide)-poly(ethylene oxide) triblock copolymer), polyethyleneoxide (Polyox), polyvinyl pyrrolidone-vinylacetate copolymer (PVP/VA copolymer; Luviskol VA, Plasdone S PVP/VA), polyvinyl pyrrolidone (PVP; K-15~K-120), polyquaternium-11 (Gafquat 755N), polyquaternium-39 (Merquat plus 3330), carboxypolymethylene (Carbomer, Carbopol), hydroxypropyl methyl cellulose, hydroxyethyl cellulose, hydroxypropyl cellulose, starch, gelatin, sodium alginate and the like, and preferably, it may be hydroxypropyl methyl cellulose, polyvinyl pyrrolidone or a mixture thereof.

According to one embodiment of the present invention, a weight ratio of the water-soluble polymer and the water-insoluble polymer included in the backing layer (water-soluble polymer:water-insoluble polymer) may be 1:4 to 4:1, preferably 1.5:4 to 3.5:4.

When the water-soluble polymer and the water-insoluble polymer are in the above-mentioned weight ratio, the patch can be degraded well when removing the patch after use while maintaining the structure of the patch stably.

The backing layer can be added with various plasticizers for the same reasons as the drug layer. In addition to the above-mentioned plasticizers, propylene glycol, glycerin and polyethylene glycol, more kinds of plasticizers can be used depending on the solvent used, and castor oil and hydrogenated castor oil can also be used.

A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

In addition to the drug layer and the backing layer, the patch for attaching to teeth or a surrounding part of the teeth of the present invention may selectively further include a layer between the drug layer and the backing layer or each of the outside of the layers depending on the purpose.

According to one embodiment of the present invention, the patch for attaching to teeth or a surrounding part of teeth of the present invention can be easily removed from teeth by tooth brushing alone after use, without stripping off the backing layer separately.

As a result of brushing the patch according to the present invention for 3 min at a rate of 90 times per min back and forth at a load of 250 g, washing the patch with distilled water while collecting the wash solution, and then checking the solution, a dry weight of the residue of the patch filtered through a 1 mm-mesh sieve was just less than 2 wt % based on the total weight of the backing layer. The tooth-attachable patch of the prevent invention can be easily removed by brushing alone after use.

The patch of the present invention including the drug layer and the backing layer can be attached to teeth for use. In another embodiment, the patch can be attached to teeth or a surrounding part of teeth depending on the purpose of use. The term "surrounding part of teeth or surrounding tissue" used herein may include both the portion of the gum that is in contact with teeth and the portion of the mouth that can be in contact with a toothbrush in the process of tooth brushing even if it is somewhat distant from teeth.

The "degradation" means that one large piece is divided into smaller pieces or split apart. The disassembled pieces of the present invention may have a certain size, but may be divided into various sizes depending on external force or pressure. If a word has the meaning of being divided into several parts, it can be included in the scope of identity with the "degradation" of the present invention.

The term "patch" used herein means an adhesive-type formulation containing a specific component, and the shape or structure of the patch is not particularly limited.

Further, the tooth-attachable patch according to the present invention can be manufactured in accordance with the methods disclosed in Korean Patent No. 10-0816250, U.S. Pat. Nos. 6,689,344, 6,682,721, 6,780,401 and the like.

In another embodiment, the present inventors found the fact that the backing layer of the patch containing the water-insoluble polymer and the water-soluble polymer, especially HPMC can be easily degraded and removed by the pressure such as the brushing alone after use, thereby completing the present invention.

In particular, after study for a long period, the inventors of the present invention found the fact that when the water-soluble polymer is hydroxypropyl methylcellulose (HPMC), the polymer can provide excellent removability and also excellent use sensation without foreign body sensation after tooth brushing, compared to the case of using other water-soluble polymers.

The present invention provides a patch for attaching to teeth or a surrounding part of teeth, which comprises: a drug layer for delivering drugs to teeth according to one embodiment of the present invention; and a backing layer positioned on the opposite side of a tooth attachment surface of the drug layer, and including a water-insoluble polymer and hydroxypropyl methyl cellulose (HPMC), wherein the backing layer is degraded by tooth brushing.

The term "tooth brushing" used herein is also called brushing, and means a process of removing residues left in the surface of teeth or foreign matters in the gap of teeth.

The present inventors have studied to manufacture the backing layer, which have been manufactured only as water-insoluble in the art, in the form that it can be degraded by tooth brushing without stripping off the used drug backing layer, and as a result, found that particularly, when hydroxypropyl methylcellulose (HPMC) is used, it is particularly advantageous to achieve the object of the present invention.

The drug layer of the patch according to another embodiment of the present invention is a dry type in which the drug layer has no or weak adhesion strength in a dry condition, but when it is hydrated by a small amount of water at the site where the whitener is desired to function, it begins to have adhesion strength and to release the whitener as it begins to be hydrated. However, it can also be used as a gel type that can be attached to teeth by its own viscosity. The polymer which can be used to the drug layer should have hydrophilicity or at least partial hydrophilicity. The polymer mainly used may be polyalkyl vinyl ether-maleic acid copolymer (PVM/MA copolymer; Gantrez AN 119, AN 139, S-97), polyvinyl alcohol, polyacrylic acid, poloxamer 407 (Pluronic, polyethylene oxide)-poly(propylene oxide)-poly(ethylene oxide) triblock copolymer), polyethyleneoxide (Polyox), polyvinyl pyrrolidone-vinyl acetate copolymer (PVP/VA copolymer; Luviskol VA, Plasdone S PVP/VA), polyvinyl pyrrolidone (PVP; K-15-K-120), polyquaternium-11 (Gafquat 755N), polyquaternium-39 (Merquat plus 3330), carboxypolymethylene (Carbomer, Carbopol), hydroxypropyl methylcellulose, hydroxyethyl cellulose, hydroxypropyl cellulose, starch, gelatin, sodium alginate alone or a mixture thereof. A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

A matter for tooth attachment should be flexible enough to be attached directly to teeth and be easily shaped according to the flexion of teeth. Depending on the polymer, this flexibility may be poor, so a suitable plasticizer may be added. Suitable plasticizer may vary depending on the kind of polymer and its prescription, and polypropylene glycol, glycerin or polyethylene glycol is generally used, and all of them also can be used.

Further, in the drug layer, a chelating agent such as EDTA or sodium citrate may be added for the purpose of improving the temporal stability of peroxide.

It has been recognized in the art that the backing layer, which is used to protect the drug layer from physical or chemical contact such as saliva and contact in the oral cavity or to maintain a product shape is preferably a water-insoluble polymer in order to serve as a backing layer, and it is stripped off after use of the backing layer. However, unlike such common sense in the art, the inventors of the present invention designed a method for using the backing layer, which can be easily removed by simply tooth brushing alone without stripping off the backing layer because the backing layer includes HPMC.

As described above, the term "backing layer" used herein means a layer playing a role in preventing contact with the skin in the oral cavity other than teeth.

In one embodiment of the present invention, the backing layer may include a water-insoluble polymer commonly used for an oral film, and for example, it may be cellulose acetate phthalate, shellac, polyvinyl acetate, ethyl cellulose, polymethyl methacrylate methacryloyl ethyl betaine/methacrylate copolymer (Yukaformer: manufactured by Mitsubishi), methacrylic acid copolymer (Eudragit L 100, Eudragit L 12.5, Eudragit L 100-55, Eudragit L 30D-55), aminoalkyl methacrylate copolymer (Eudragit E 100, Eudragit E 12.5, Eudragit RL 100, Eudragit RL 30D) and the like. Preferably, the water-insoluble polymer may be ethyl cellulose, which has excellent compatibility with HPMC and can be removed after tooth brushing without foreign body sensation mostly.

In addition, the backing layer of the tooth-attachable patch of the present invention also includes hydroxypropyl methylcellulose (HPMC) together. The HPMC has a characteristic of being bulky when soaked in water. The inventors of the present invention found that when using the HPMC together with a water-insoluble polymer, degradation ability of the backing layer including the water-insoluble polymer becomes larger compared to the case of using other water-soluble polymers. When tooth brushing in the state that the backing layer is attached to the surface of teeth, removability was better than the case of using other water-soluble polymer, and the backing layer was degraded more finely, thereby reducing foreign body sensation and having more excellent use sensation in the process of tooth brushing That have been confirmed through specific experiments.

The HPMC is defined as HPMC1828, HPMC2208(K), HPMC2906(F), HPMC2910(E) depending on the ratio of —$OCH_3$, —$OCH_2CH(CH_3)OH$ in United States Pharmacopeia (USP), and the kind of the HPMC used in the backing layer of the present invention is not particularly limited.

According to one embodiment of the present invention, a weight ratio of the water-insoluble polymer and the HPMC included in the backing layer of the patch (water-insoluble polymer:HPMC) may be 1:0.2 to 4, and preferably 1:0.5 to 2. If the weight ratio of the HPMC is less than the above range, excessive pressure or force should be applied to degrade the water-insoluble polymer by tooth brushing, and even if the polymer is degraded, the particle size is large, so that the foreign body sensation may be relatively large. If the ratio is over the above range, there may be a problem that the drug contained in the drug layer may be transferred to the backing layer and absorbed, thereby rendering it unable to function properly as a backing layer, and even during use of the patch, the saliva may be absorbed excessively and the structure may collapse, rendering it unable to function properly as a backing layer.

The backing layer can be added with various plasticizers for the same reasons as the drug layer. In addition to the above-mentioned plasticizers, propylene glycol, glycerin and polyethylene glycol, more kinds of plasticizers can be used depending on the solvent used, and castor oil and hydrogenated castor oil can also be used.

A solvent for the polymer may be primarily water, ethanol alone or a mixture thereof, and other organic solvents, for example, ethyl acetate, methylene chloride, isopropyl alcohol, acetonitrile alone or a mixture thereof at a controlled ratio.

In addition to the drug layer and the backing layer, the tooth-attachable patch of the present invention may selectively further include a layer between the drug layer and the backing layer or each of the outside of the layers depending on the purpose.

According to one embodiment of the present invention, the tooth-attachable patch of the present invention can be easily detached from teeth by tooth brushing alone after use, without stripping off the backing layer separately.

Among the polymers contained in the backing layer, when a mixture of the water-insoluble polymer and the HPMC is used, removal by brushing may be easier, compared to the case of using only the water-insoluble polymer. Further, the backing layer may be degraded into smaller particles, compared to the case of using other water-soluble polymers. As a result of brushing the patch according to the present invention for 3 min at a rate of 90 times per min back and forth at a load of 250 g, collecting wash solution while washing the patch with distilled water, and then checking the solution, a dry weight of the residue of the patch filtered through a 0.5 μm-mesh sieve was just less than 5 wt %, preferably less than 4.5 wt %, more preferably less than 4 wt %, based on the total weight of the backing layer. The tooth-attachable patch of the prevent invention can be easily removed by brushing alone after use.

The tooth-attachable patch of the prevent invention can be easily removed by brushing alone after use.

The patch 1 according to one embodiment of the present invention comprises a drug layer 10 in contact with teeth or a surrounding part of teeth and a backing layer 20 positioned on one side of the drug layer 10, and in one side of the backing layer 20, a breakable portion 30 is formed.

The breakable portion 30 means a portion processed and treated such that the backing layer 20 can be degraded into a predetermined size by an external force. If the backing layer 20 is broken, the shape of the breakable portion 30 is not particularly limited. For example, the breakable portion 30 may include any shape that the breakable portion 30 is thinner than other portions of the backing layer 20, and the backing layer 20 is allowed to be easily broken along this portion. Preferably, it may include a shape such as prominence and depression 31. In another embodiment, the breakable portion 30 may be formed with a bubble 32 so that the backing layer 20 is allowed to be easily broken.

The breakable portion 30 means a portion that is thinner than other portions of the backing layer 20 but has a certain thickness, and can be distinguished from a pit or a hole formed in the backing layer. Namely, the structure in which a pit or a hole is formed in the backing layer of the patch and the drug component of the drug layer 10 is moved through the hole of the backing layer is not included in the structure of the "breakable portion" of the present invention.

In the case that a pit or a hole is formed in the backing layer and the component of the drug layer 10 is moved through the pit or the hole of the backing layer, the amount of the drug released through the backing layer may increase resulting in loss of drug to be delivered to teeth or a surrounding part of teeth. In the aspect to achieve the original purpose of the backing layer 20, the breakable portion preferably has a structure in which the drug of the drug layer 10 cannot be move across the backing layer.

According to one embodiment of the present invention, the breakable portion 30 may include a bubble 32. The prominence and depression structure may have a concave portion 311 in a depth of more than 0 μm and 30 μm or less based on a convex portion.

Pieces degraded through the breakable portion 30 may preferably have the size of about 1 mm in length and width.

The term "break" used herein means that the backing layer is separated into two or more parts, and the patch of the present invention can be easily broken along the breakable portion 30 formed in the backing layer 20. Herein, the meaning that the backing layer 20 is broken is used as a concept including that the backing layer 20 is degraded into a plurality of pieces.

The "degradation" means that one large piece is divided into smaller pieces or split apart. The disassembled pieces of the present invention may have a certain size, but may be divided into various sizes depending on external force or pressure.

Advantageous Effects

The tooth-attachable patch of the present invention is an easy-to-use type tooth-attachable patch that selectively releases a drug to the surface of teeth without striping off the backing layer.

The patch of the present invention can be degraded and removed by only light tooth brushing.

The patch of the present invention may include various drugs depending on its purpose.

The patch of the present invention including HPMC in a backing layer have little foreign body sensation because it can make the particle size of the patch remained in the mouth after tooth brushing small, and also can provide excellent use sensation.

DESCRIPTION OF DRAWINGS

Other objects and aspects of the present invention will become apparent from the following descriptions of the embodiments with reference to the accompanying drawings in which.

The accompanying drawings illustrate a preferred embodiment of the present invention and together with the foregoing disclosure, serve to provide further understanding of the technical spirit of the present invention, and thus, the present invention is not construed as being limited to the drawing.

BEST MODE

Figure 1:
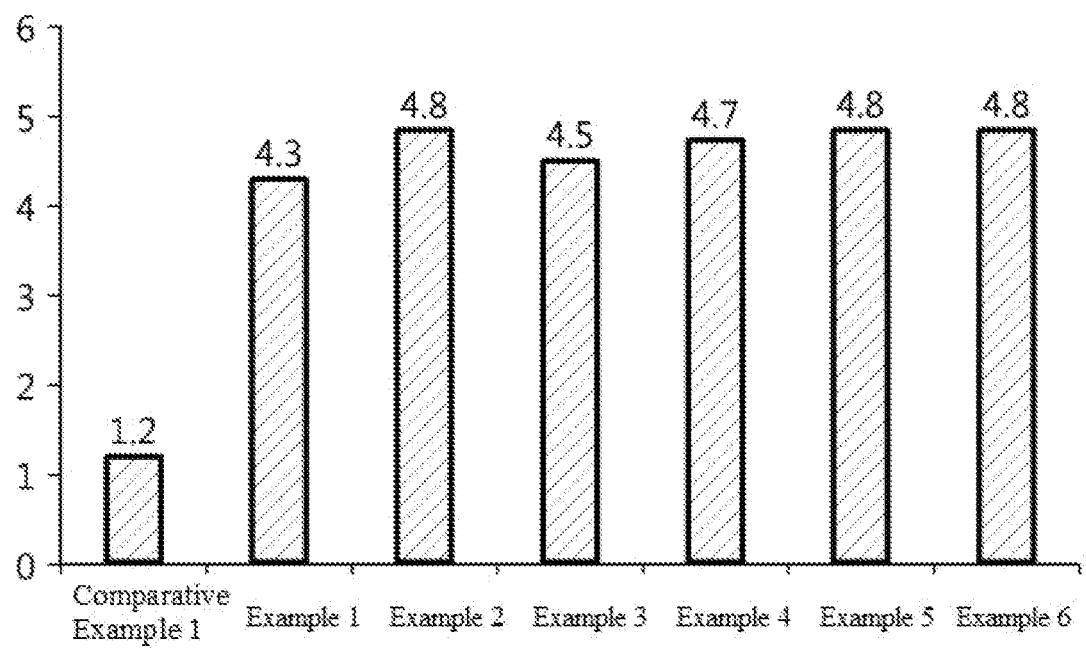
FIG. 1 shows the result of the survey for the convenience of removal of the patches of Comparative Examples and Examples. As can be seen from FIG. 1, higher score was obtained from users who used the patches of Examples.
Figure 2:
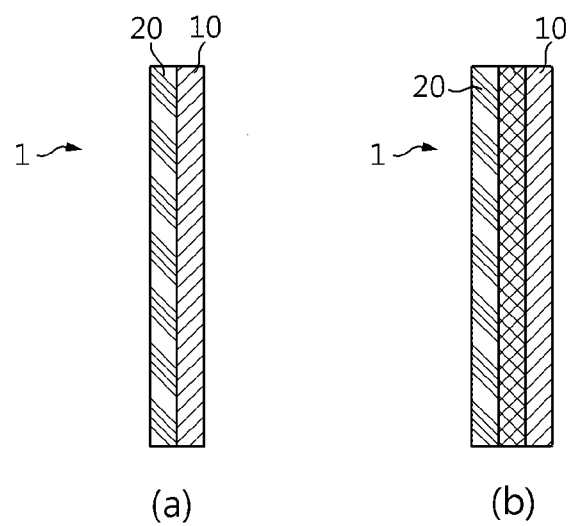
FIG. 2 is a drawing prefiguratively showing the tooth-attachable patch 1 of the present invention. As prefiguratively shown in FIG. 2a, the patch may include a drug layer 10 and a backing layer 20, and as shown in FIG. 2b, the patch may include another layer separately between the drug layer 10 and the backing layer 20 depending on its purpose.

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

MODE FOR DISCLOSURE

Preparative Example 1

<Preparation of Patch for Tooth Whitening>

Patches for tooth whitening of Comparative Examples having composition of the following Table 1 and Patches for tooth whitening of Examples having composition of the following Table 2 were prepared according to the method for preparing a backing layer and a drug reservoir layer in Preparative Example 1 of Korean Patent No. 10-0816250.

TABLE 1

|  |  | Comparative Example 1 |  | Comparative Example 2 |  |
| --- | --- | --- | --- | --- | --- |
| Drug layer | Hydrogen peroxide | 2.9% | Hydrogen peroxide | 2.9% |
|  | Povidone | 19.0% | Povidone | 19.0% |
|  | Glycerin | 3.0% | Glycerin | 3.0% |
|  | Pullulan | 1.0% | Pullulan | 1.0% |
|  | SPAN80 | 5.0% | SPAN80 | 5.0% |
|  | Water etc. | to 100% | Water etc. | to 100% |
| Backing layer | Ethyl Cellulose | 15.0% | Povidone | 15.0% |
|  | Castor oil | 10.0% | glycerin | 3.0% |
|  | Ethanol etc. | to 100% | Pullulan | 1.0% |
|  |  |  | Water etc. | to 100% |

TABLE 2

|  |  | Example 1 | | Example 2 | | Example 3 | | Example 4 | |
| --- | --- | --- | --- | --- | --- | --- | --- | --- | --- |
| Drug layer | Hydrogen peroxide | 2.9% | Hydrogen peroxide | 2.9% | Hydrogen peroxide | 2.9% | Hydrogen peroxide | 2.9% |
|  | Povidone | 19.0% | Povidone | 19.0% | Povidone | 19.0% | Povidone | 19.0% |
|  | Glycerin | 3.0% | Glycerin | 3.0% | Glycerin | 3.0% | Glycerin | 3.0% |
|  | Pullulan | 1.0% | Pullulan | 1.0% | Pullulan | 1.0% | Pullulan | 1.0% |
|  | SPAN80 | 5.0% | SPAN80 | 5.0% | SPAN80 | 5.0% | SPAN80 | 5.0% |
|  | Water etc. | to 100% | Water etc. | to 100% | Water etc. | to 100% | Water etc. | to 100% |
| Backing layer | Ethyl Cellulose | 12.0% | Ethyl Cellulose | 3.0% | Ethyl Cellulose | 12.0% | Ethyl Cellulose | 3.0% |
|  | Hydroxypropyl methylcellulose | 3.0% | Hydroxypropyl methylcellulose | 12.0% | Povidone | 3.0% | Povidone | 12.0% |
|  | Castor oil | 15.0% | Castor oil | 5.0% | Castor oil | 15.0% | Castor oil | 5.0% |
|  | SPAN80 | 5.0% | SPAN80 | 15.0% | SPAN80 | 5.0% | SPAN80 | 15.0% |
|  | Ethanol etc. | to 100% | Ethanol etc. | to 100% | Ethanol etc. | to 100% | Ethanol etc. | to 100% |

TABLE 3

|  |  | Example 5 | | Example 6 | |
| --- | --- | --- | --- | --- | --- |
| Drug layer | Potassium phosphate monobasic | 2.0% | Bamboo salt | 3.0% |
|  | Potassium phosphate dibasic | 3.0% | Titrated Extract of *Zea Mays* L. unsaponifiable fraction | 0.5% |
|  | Povidone | 19.0% | Povidone | 19.0% |
|  | Glycerin | 3.0% | Glycerin | 3.0% |
|  | Pullulan | 1.0% | Pullulan | 1.0% |
|  | SPAN80 | 5.0% | SPAN80 | 5.0% |
|  | Water etc. | to 100% | Water etc. | to 100% |
| Backing layer | Ethyl Cellulose | 6.0% | Ethyl Cellulose | 7.0% |
|  | Hydroxypropyl methylcellulose | 8.0% | Hydroxypropyl methylcellulose | 8.0% |
|  | Castor oil | 15.0% | Castor oil | 5.0% |
|  | SPAN80 | 5.0% | SPAN80 | 15.0% |
|  | Ethanol etc. | to 100% | Ethanol etc. | to 100% |

<Survey for Removability>

Survey for removal convenience was conducted to patches of Comparative Example 1 and Examples 1 to 6 which need a removal process after use, except a patch of Comparative Example 2 which melts away during use. Each of the patches of Comparative Example 1 and Examples 1 to 6 was attached to 30 responders for 15 min according to the group, and then the patch of Comparative Example 1 or Examples 1 to 6 was removed by tooth brushing. Then, each group changed the products and then responded to a questionnaire for removal convenience.

—Criteria for Survey Response—

5: Removal is very convenient and there is no clotting in a toothbrush.

4: Removal is convenient but there is little residue in a toothbrush.

3: Removal is inconvenient and there is inconvenience due to residue in a toothbrush.

2: Removal is inconvenient and there are many residues in a toothbrush.

1: Removal is very inconvenient and there are so many residues in a toothbrush.

As can be seen from FIG. 1, in the case of Comparative Example 1, the majority of investigators evaluated that there were many lumpy residues in the toothbrush and removal was very inconvenient. However, the majority of investigators used the patches of Examples of the present invention evaluated that removal by tooth brushing was convenient and there was little residue.

It was confirmed that the tooth patch of the present invention was conveniently removed when removed by tooth brushing after use and the toothbrush was clean without lumping and clotting.

<Evaluation of Degradation by Tooth Brushing>

Two sets of Comparative Example 1 and Examples 1 to 6 were prepared. Each patch of one set was shaken in distilled water for 30 min to leave only a backing layer, dried and then weight of the patch was measured. Each patch of the other set was attached to a slide glass, stored in 37° C., 85% humidity environment for 30 min, and then brushed for 3 min using a brushing machine at a rate of 90 times per min back and forth at a load of 250 g. Then, the slide glass, the brushing chamber and the toothbrush were separated, and washed with distilled water while collecting the washing solution. The collected washing solution was filtered through a 1 mm-mesh sieve, and residue was dried and weighed to calculate a ratio of the residue based on the total weight of the backing layer.

TABLE 4

|  | Comparative Exam. 1 | Exam. 1 | Exam. 2 | Exam. 3 | Exam. 4 | Exam. 5 | Exam. 6 |
|---|---|---|---|---|---|---|---|
| Residue ratio (wt %) | 98.6 | 1.6 | 0.8 | 1.9 | 0.6 | 0.5 | 0.4 |

As can be seen from Table 4, it was confirmed that the patch of Comparative Example has a residue ratio of 98% or more, which is hardly degraded by tooth brushing. However, it was confirmed that the patch of the present invention having a backing layer including a water-soluble polymer has a residue ratio of less than 2%, which is mostly degraded by tooth brushing.

Preparative Example 2

<Preparation of Patch for Tooth Whitening>

Patches for tooth whitening of Comparative Examples having composition of the following Table 5 and Patches for tooth whitening of Examples having composition of the following Table 5 and Table 6 were prepared.

TABLE 5

|  | Comparative Example 3 |  | Example 7 |  | Example 8 |  |
|---|---|---|---|---|---|---|
| Drug layer | Hydrogen peroxide | 2.9% | Hydrogen peroxide | 2.9% | Hydrogen peroxide | 2.9% |
|  | Povidone | 19.0% | Povidone | 19.0% | Povidone | 19.0% |
|  | Glycerin | 3.0% | Glycerin | 3.0% | Glycerin | 3.0% |
|  | Pullulan | 1.0% | Pullulan | 1.0% | Pullulan | 1.0% |
|  | Water etc. | to 100% | Water etc. | to 100% | Water etc. | to 100% |
| Backing layer | Ethyl Cellulose | 20.0% | Ethyl Cellulose | 10.0% | Ethyl Cellulose | 10.0% |
|  |  |  | Povidone | 10.0% | Poloxamer | 10.0% |
|  |  |  | SPAN80 | 5.0% | SPAN80 | 5.0% |
|  | Castor oil | 10.0% | Castor oil | 5.0% | Castor oil | 5.0% |
|  | Ethanol etc. | to 100% | Ethanol etc. | to 100% | Ethanol etc. | to 100% |

TABLE 6

|  | Example 9 |  | Example 10 |  | Example 11 |  |
|---|---|---|---|---|---|---|
| Drug layer | Hydrogen peroxide | 2.9% | Potassium phosphate monobasic | 2.0% | Bamboo salt | 3.0% |
|  |  |  | Potassium phosphate dibasic | 3.0% | Titrated Extract of *Zea Mays* L. unsaponifiable fraction | 0.5% |
|  | Povidone | 19.0% | Povidone | 19.0% | Povidone | 19.0% |
|  | Glycerin | 3.0% | glycerin | 3.0% | glycerin | 3.0% |
|  | Pullulan | 1.0% | Pullulan | 1.0% | Pullulan | 1.0% |
|  |  |  | SPAN80 | 5.0% | SPAN80 | 5.0% |
|  | Water etc. | to 100% | Water etc. | to 100% | Water etc. | to 100% |
| Backing layer | Ethyl Cellulose | 10.0% | Ethyl Cellulose | 6.0% | Ethyl Cellulose | 7.0% |
|  | HPMC 2910 | 10.0% | HPMC 2910 | 8.0% | HPMC 2910 | 8.0% |
|  | SPAN80 | 5.0% | Castor oil | 15.0% | Castor oil | 5.0% |
|  | Castor oil | 5.0% | SPAN80 | 5.0% | SPAN80 | 15.0% |
|  | Ethanol etc. | to 100% | Ethanol etc. | to 100% | Ethanol etc. | to 100% |

*HPMC: HYDROXYPROPYL METHYLCELLULOSE

Patches for tooth whitening having composition of Table 5 and Table 6 were prepared according to the method for preparing a backing layer and a drug reservoir layer in Preparative Example 1 of Korean Patent No. 10-0816250. HPMC (AN6 from Samsung fine chemical Co., Ltd) used in Examples 9 to 11 was 2910 and its viscosity type was 6 cPs.

<Survey for Removability>

Survey for removal convenience was conducted to patches of Comparative Example 3 and Examples 7 to 11. Each of the patches of Comparative Example 3 and Examples 7 to 11 was attached to 30 responders for 30 min according to the group, and then the patch of Comparative Example 3 or Examples 7 to 11 was removed by tooth brushing. Then, each group changed the products and then responded to a questionnaire for removal convenience.

—Criteria for Survey Response—

5: Removal is very convenient and there is no residue in a toothbrush.

4: Removal is convenient but there is little residue in a toothbrush.

3: Removal is inconvenient and there is inconvenience due to residue in a toothbrush.

2: Removal is inconvenient and there are many residues in a toothbrush.

1: Removal is very inconvenient and there are so many residues in a toothbrush.

Figure 3:
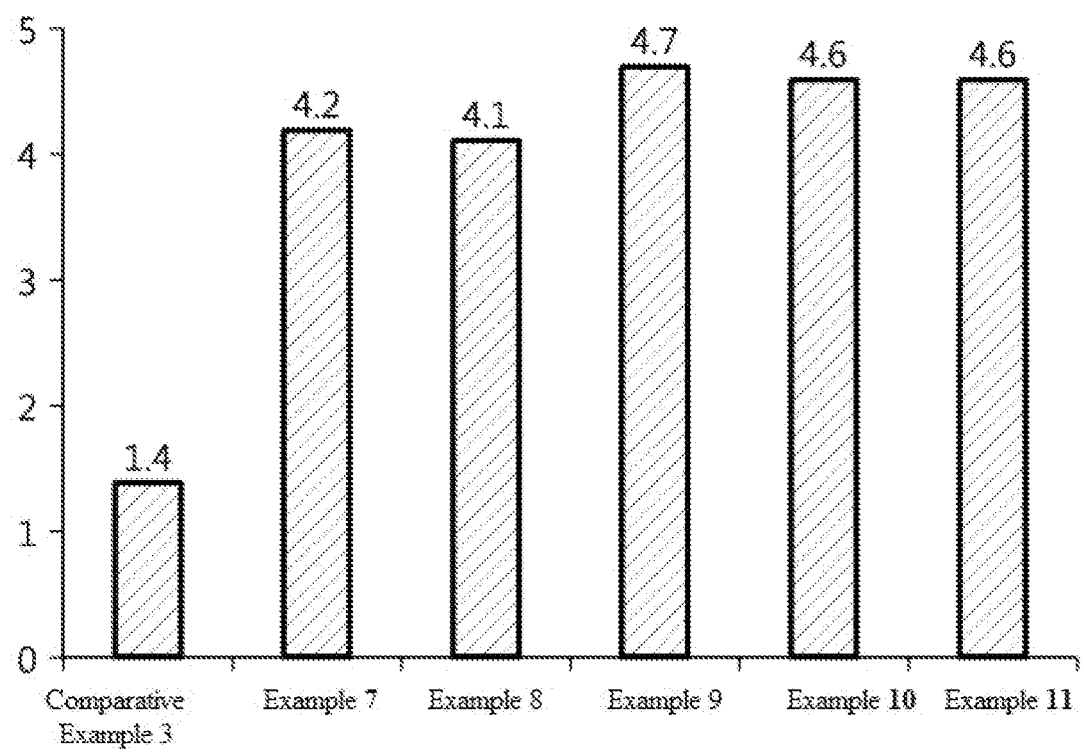
FIG. 3 is a graph showing the result of evaluating removability of the patches of Table 5 and Table 6.
Figure 4:
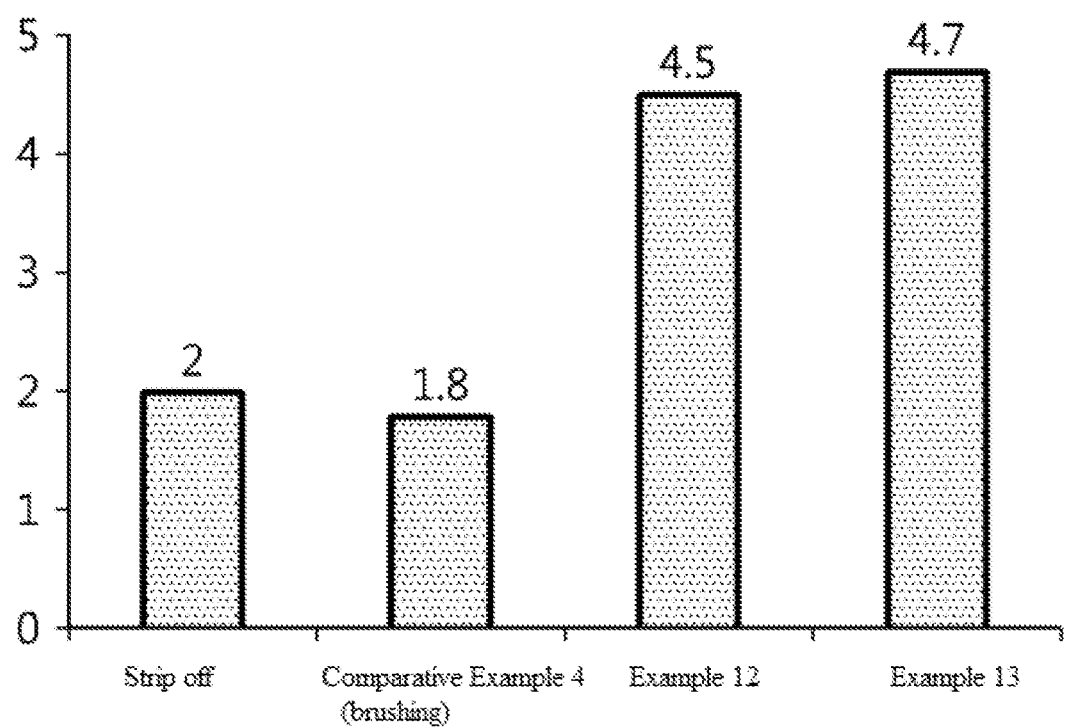
FIG. 4 is a graph showing the result of evaluating removability of the patch including a breakable portion and the patch not including a breakable portion of the present invention.
Figure 5:
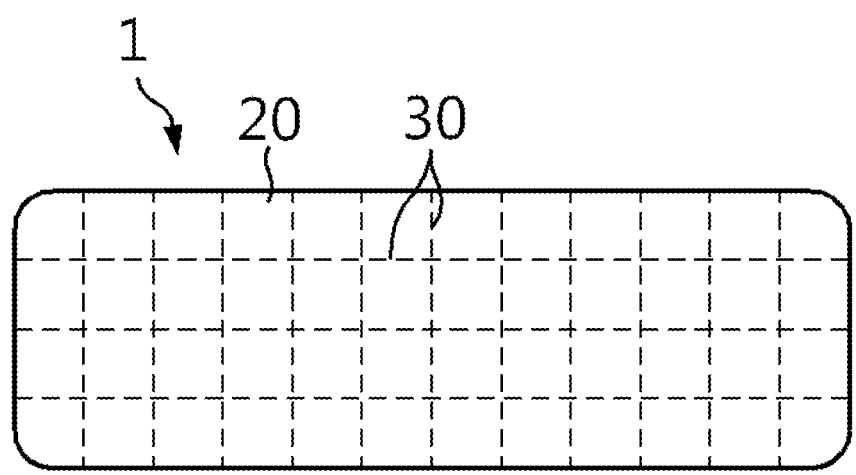
FIG. 5 is a drawing prefiguratively showing the patch 1 including a breakable portion 30 of the present invention.
Figure 6:
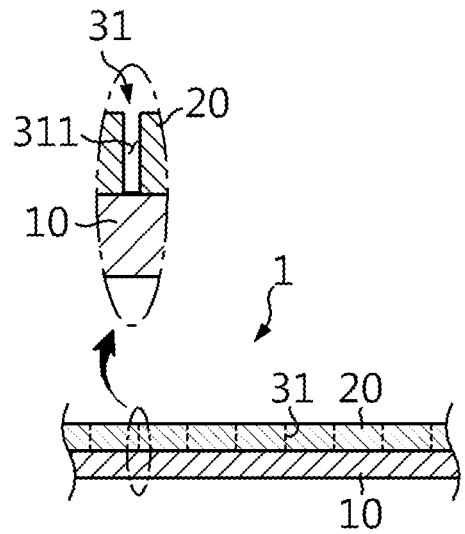
FIG. 6 is a drawing prefiguratively showing an example that the breakable portion 30 includes prominence and depression 31 in the patch 1 including the breakable portion 30 of the present invention.
Figure 6:
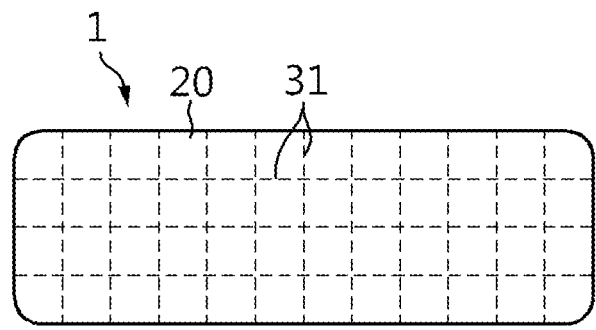
Figure 7:
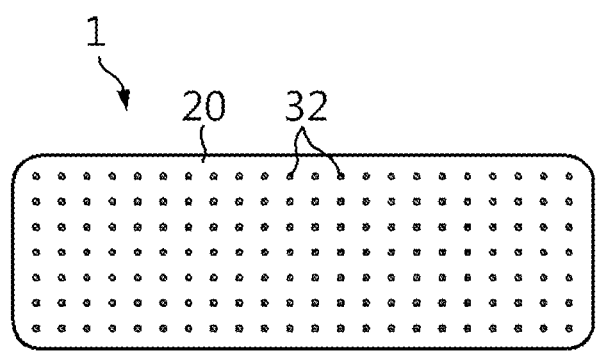
FIG. 7 a drawing prefiguratively showing an example that the breakable portion 30 includes a bubble 32 in the patch 1 including the breakable portion 30 of the present invention.
Figure 7:
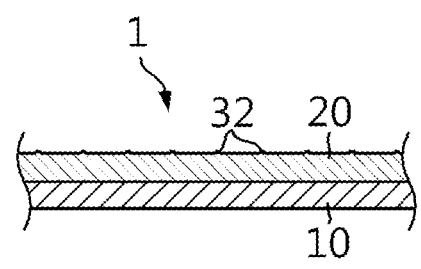

As can be seen from FIG. 3, when the user brushed teeth at 30 min after attaching the patch of Comparative Example 3, it was evaluated that removal was generally inconvenient and there was many residues.

However, the patches of Examples 7 to 11 mostly got 4 points or more, and most of them were evaluated that removal was convenient.

It was confirmed that among them, the patches of Examples 9 to 11 used HPMC as a water-soluble polymer had especially excellent removability.

<Evaluation of Degradation by Tooth Brushing>

Two sets of Comparative Example 3 and Examples 7 to 11 were prepared. Each patch of one set was shaken in distilled water for 30 min to leave only a backing layer, dried and then weight of the patch was measured. Each patch of the other set was attached to a slide glass, stored in 37° C., 85% humidity environment for 30 min, and then brushed for 3 min using a brushing machine at a rate of 90 times per min back and forth at a load of 250 g. Then, the slide glass, the brushing chamber and the toothbrush were separated, and washed with distilled water while collecting the washing solution. The collected washing solution was filtered through a 500 μm-mesh sieve, and residue was dried and weighed to calculate a ratio of the residue based on the total weight of the backing layer.

TABLE 7

|  | Comparative Exam. 3 | Exam. 7 | Exam. 8 | Exam. 9 | Exam. 10 | Exam. 11 |
|---|---|---|---|---|---|---|
| Residue ratio (wt %) | 97.9 | 15.6 | 15.9 | 3.7 | 3.3 | 3.8 |

As can be seen from Table 7, it was confirmed that the patch of Comparative Example 3 was hardly degraded by tooth brushing, and could not pass through the 500 μm-mesh sieve. Namely, about 98 wt % or more of the patch was remained on the sieve.

However, the patches of Examples 7 and 8 were remained about 15 wt % to 20 wt %, and most of the patches of Examples 9 to 11 were finely degraded to pass through the sieve, and about 5 wt % or less thereof was remained on the sieve.

As can be seen from the above results, it can be found that among water-soluble polymers, especially HPMC, unlike other water-soluble polymers, allows the backing layer to be easily degraded by tooth brushing.

INDUSTRIAL APPLICABILITY

The present invention can provide a patch which can be easily removed by tooth brushing after being attached to teeth or a surrounding part of teeth.

The present invention has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A patch for attaching to teeth or a surrounding part of teeth, which comprises:

a drug layer for delivering drugs to teeth; and a backing layer positioned on the opposite side of a tooth attachment surface of the drug layer, and including both a water-soluble polymer and a water-insoluble polymer, wherein a weight ratio of the water-soluble polymer to the water-insoluble polymer included in the backing layer is 1:4 to 4:1.

2. The patch for attaching to teeth or a surrounding part of teeth of claim 1, wherein the water-soluble polymer comprises at least one selected from the group consisting of polyalkyl vinyl ether-maleic acid copolymer, polyvinyl alcohol, polyacrylic acid, poloxamer 407, polyethyleneoxide, polyvinyl pyrrolidone-vinyl acetate copolymer, polyvinyl pyrrolidone, polyquaternium-11, polyquaternium-39, carboxypolymethylene, hydroxypropyl methylcellulose, hydroxyethyl cellulose, hydroxypropyl cellulose, starch, gelatin, and sodium alginate.

3. The patch for attaching to teeth or a surrounding part of teeth of claim 2, wherein the water-soluble polymer is hydroxypropyl methyl cellulose, polyvinyl pyrrolidone or a mixture thereof.

4. The patch for attaching to teeth or a surrounding part of teeth of claim 1, wherein the drug layer comprises at least one selected from the group consisting of ingredients for whitening teeth, ingredients for preventing or improving sensitive teeth, ingredients for preventing cavities, and ingredients for preventing periodontal disease.

5. The patch for attaching to teeth or a surrounding part of teeth of claim 4, wherein the ingredients for whitening teeth are:

at least one peroxide selected from the group consisting of hydrogen peroxide, carbamide peroxide, calcium peroxide, sodium percarbonate, sodium perborate, tetrasodium pyrophosphate peroxidate and a mixture thereof;

at least one polyphosphate selected from the group consisting of tetrasodium pyrophosphate, sodium acid pyrophosphate, sodium hexametaphosphate, sodium tripolyphosphate, sodium potassium tripolyphosphate, tetrapotassium pyrophosphate, ultra-metaphosphate as ultra-phosphate, acidic sodium polyphosphate, and a mixture thereof; or a mixture thereof.

6. The patch for attaching to teeth or a surrounding part of teeth of claim 4, wherein the ingredients for preventing or improving sensitive teeth or cavities are at least one selected from the group consisting of strontium chloride, calcium carbonate, sodium citrate, sodium fluoride, silica, hydroxyapatite, potassium nitrate, and potassium phosphate.

7. The patch for attaching to teeth or a surrounding part of teeth of claim 1, wherein the patch is capable of being degraded by tooth brushing, wherein a dry weight of the residue of the patch filtered through a 1 mm mesh after brushing the patch for 3 min at a rate of 90 times per min back and forth at a load of 250 g is less than 2 wt % based on the total weight of the backing layer before brushing.

8. The patch for attaching to teeth or a surrounding part of teeth of claim 1, wherein the backing layer has a breakable portion.

9. The patch for attaching to teeth or a surrounding part of teeth of claim 8, wherein the breakable portion includes prominence and depression or bubbles.

10. The patch for attaching to teeth or a surrounding part of teeth of claim 9, wherein the prominence and depression has a concave portion in a depth of more than 0 μm and 30 μm or less based on a convex portion.

11. The patch for attaching to teeth or a surrounding part of teeth of claim 9, wherein the prominence and depression has a concave portion in a width of more than 0 mm and 0.1 mm or less.

12. A patch for attaching to teeth or a surrounding part of teeth, which comprises:
   a drug layer for delivering drugs to teeth; and
   a backing layer positioned on the opposite side of a tooth attachment surface of the drug layer, and including a water-insoluble polymer and hydroxypropyl methyl cellulose (HPMC),
   wherein the backing layer is capable of being degraded by tooth brushing.

13. The patch for attaching to teeth or a surrounding part of teeth of claim 12, wherein the water-insoluble polymer is at least one selected from the group consisting of cellulose acetate phthalate, shellac, polyvinyl acetate, ethyl cellulose, polymethyl methacrylate, methacryloyl ethyl betaine/methacrylate copolymer, methacrylic acid copolymer, and aminoalkyl methacrylate copolymer.

14. The patch for attaching to teeth or a surrounding part of teeth of claim 12, wherein the water-insoluble polymer is ethyl cellulose.

15. The patch for attaching to teeth or a surrounding part of teeth of claim 12, wherein a weight ratio of the water-insoluble polymer to the HPMC included in the backing layer of the patch is 1:0.2 to 4.

16. The patch for attaching to teeth or a surrounding part of teeth of claim 12, wherein a dry weight of the residue of the patch filtered through a 500 μm mesh after brushing the patch for 3 min at a rate of 90 times per min back and forth at a load of 250 g is less than 5 wt % based on the total weight of the backing layer before brushing.

17. The patch for attaching to teeth or a surrounding part of teeth of claim 12, wherein the backing layer has a breakable portion.

18. The patch for attaching to teeth or a surrounding part of teeth of claim 12, wherein the breakable portion includes prominence and depression or bubbles.

* * * * *